Figure 1:
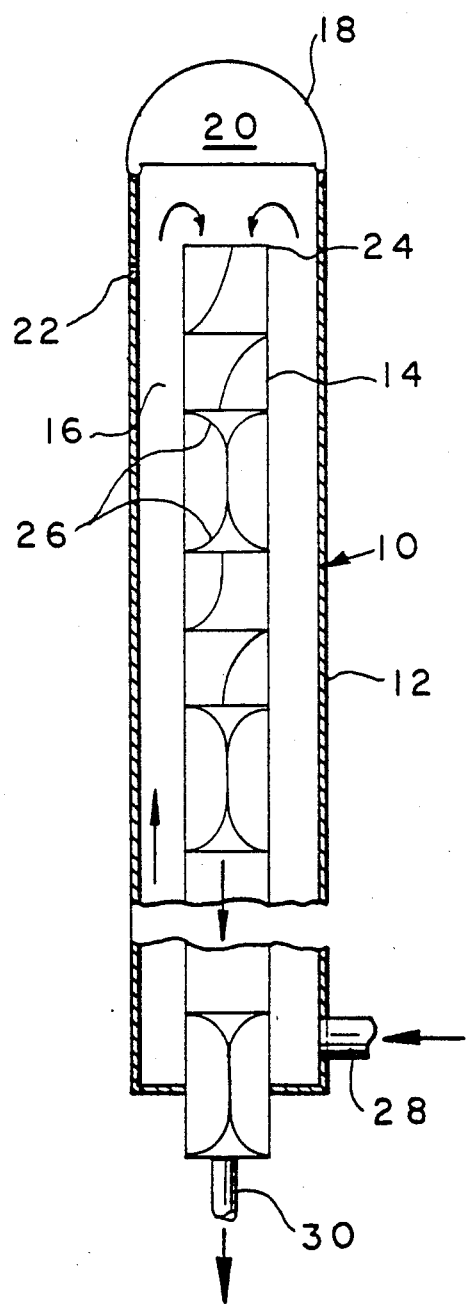
Figure 2:
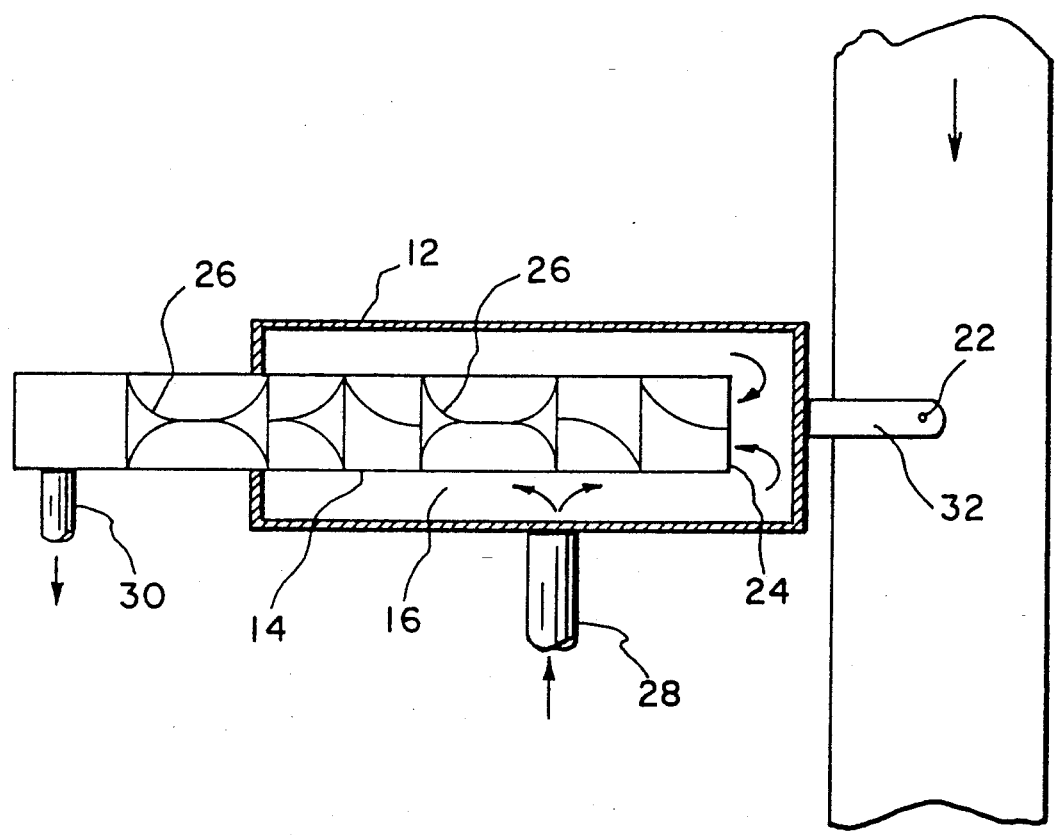
Figure 3A:
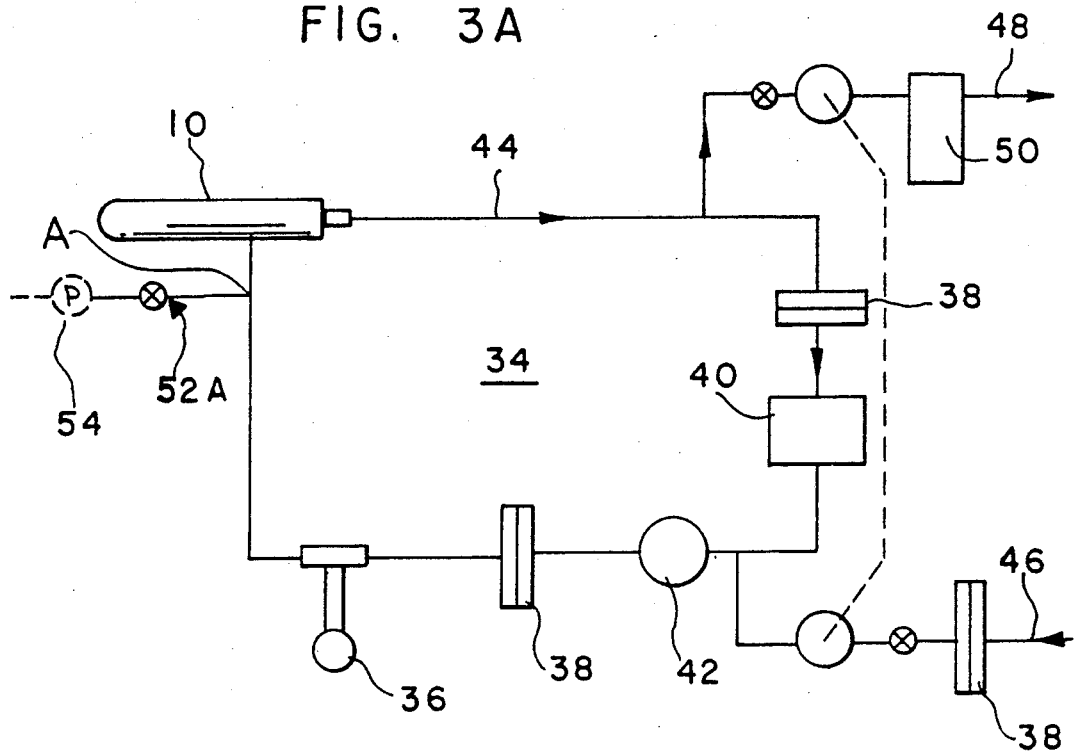
Figure 3B:
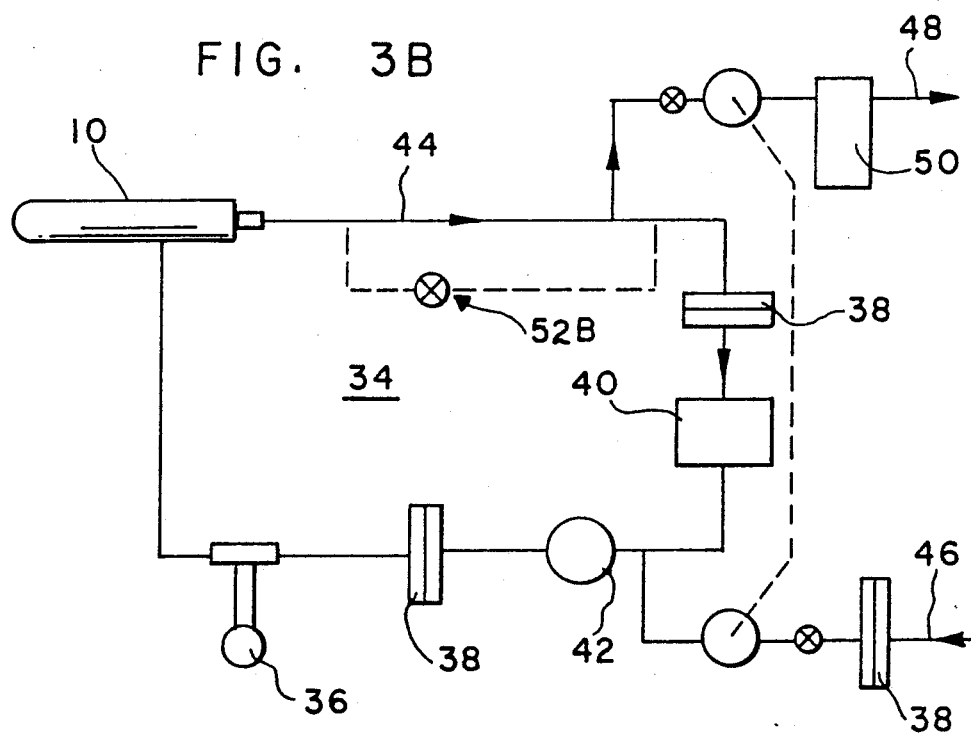

United States Patent [19]

Lawless

[11] Patent Number: 5,109,708
[45] Date of Patent: May 5, 1992

[54] SAMPLING SYSTEM AND METHOD FOR SAMPLING CONCENTRATED AEROSOLS

[75] Inventor: Philip A. Lawless, Durham, N.C.

[73] Assignee: E. I. Du Pont de Nemours and Company, Wilmington, Del.

[21] Appl. No.: 445,955

[22] Filed: Nov. 28, 1989

Related U.S. Application Data

[63] Continuation-in-part of Ser. No. 323,819, Mar. 15, 1989, abandoned.

[51] Int. Cl.⁵ .......................................... G01N 31/00
[52] U.S. Cl. ............................ 73/863.11; 73/863.83; 73/28.01
[58] Field of Search ................ 73/28, 863.11, 863.81, 73/863.83, 864.34, 864.81, 865.5, 28.01–28.05

[56] References Cited

U.S. PATENT DOCUMENTS

| | | | |
|---|---|---|---|
| 3,478,600 | 11/1969 | Lynn | 73/432 |
| 3,699,814 | 10/1972 | Kaufman | 73/421.5 |
| 3,739,180 | 6/1973 | Carlson | 250/218 |
| 3,807,233 | 4/1974 | Crawford | 73/421.5 |
| 3,901,672 | 8/1975 | Roberts | 55/387 |
| 3,986,386 | 10/1976 | Baltzer et al. | 73/28 |
| 4,361,028 | 11/1982 | Kamiya et al. | 73/28 |
| 4,586,367 | 5/1986 | Lewis | 73/116 X |
| 4,747,297 | 5/1988 | Okayama et al. | 73/28 |
| 4,756,200 | 7/1988 | Ramsner et al. | 73/863.11 |

FOREIGN PATENT DOCUMENTS 63-269036  11/1988  Japan .

*Primary Examiner*—Robert Raevis
*Attorney, Agent, or Firm*—Caroline J. Yun

[57] ABSTRACT

Sampling system and method for obtaining representative samples of aerosols in which the particulate concentration is greater than $10^6$ particles/cm³ comprising a sampling probe which operates in cooperation with a dilution system such that a sample of concentrated aerosol can be taken from the gas stream by the probe and almost simultaneously quenched and diluted to a temperature and concentration, respectively, which is acceptable to conventional measuring instruments.

4 Claims, 3 Drawing Sheets of the invention

SAMPLING SYSTEM AND METHOD FOR SAMPLING CONCENTRATED AEROSOLS

CROSS REFERENCE TO EARLIER FILED APPLICATION

This application is a continuation-in-part of application Ser. No. 07/323,819, filed on Mar. 15, 1989, and now abandoned.

BACKGROUND OF THE INVENTION

The present invention relates to an improved sampling system and method for obtaining representative samples of particles from concentrated aerosols, and, more particularly, to an improved sampling system and method for measuring the size and distribution of particles comprising aerosols in which the particle concentration of the aerosol is greater than $10^6$ particles/cm$^3$.

There are two basic approaches for measuring the size of particles entrained in a gas stream, i.e., within the aerosol. One approach is to measure the size and size distribution of the entrained particles directly in situ without actually removing a sample from the gas stream. The second approach, and the approach to which this invention is directed, is to sample the particles from the gas and then obtain the size measurement. It is critically important, however, that the particles sampled for measurement are no more or less agglomerated than those remaining in the gas, otherwise the size and size distribution values will not be representative. A highly hostile, heavily particle-laden gas stream refers herein to a gas stream having a particle concentration greater than about $10^6$ particles/cm$^3$ and a temperature which can range up to 1000° C. or higher and/or a corrosive chemical environment. A highly hostile, heavily particle-laden gas stream offers significant problems in connection with obtaining a representative sample for measurement and is undisclosed in the prior art.

For example, U.S. Pat. No. 3,478,600 describes an apparatus designed for isokinetic sampling in a laminar flow stream, i.e., the gas/particle mixture enters the receiver tube with the same velocity as the process line flow. Turbulent process flow and highly concentrated aerosols would clog the system. A 2:1 dilution ratio is maintained; and although further dilution is possible in the expanded chamber, changes in the particle size distribution may have already occurred.

U.S. Pat. No. 4,361,028 describes a system for measuring the quantity of particulates being discharged in the exhaust of a vehicular internal combustion engine. The exhaust gases are introduced into a dilution tunnel where they are mixed and diluted with clean air. A part of the diluted gas is then sampled by means of a sampling probe, and the sample is carried to a sampled gas line in which a filter is provided to collect particulates contained in the sampled gases. The quantity of particulates being discharged in the engine exhaust gases is computed on the basis of the time differential of an electric signal from a differential pressure transducer which detects the pressure drop across the filter. Nevertheless, particle size and size distribution of the sampled gas stream is not revealed and does not appear to be a factor affecting operation of the described measuring system.

SUMMARY OF THE INVENTION

The present invention is an improved system and method for obtaining representative samples of particles from aerosols either intermittently or continuously from a moving aerosol stream in which the particulate concentration of the aerosol is greater than $10^6$ particles/cm$^3$. The system comprises a sampling probe which operates in cooperation with a dilution system such that a concentrated sample of the aerosol can be taken directly from the gas stream by the probe and almost simultaneously mixed and diluted with an appropriate amount of a dilution gas to quench the gas sample, i.e., reduce chemical reactions and particle collisions and; lower the temperature of the sample; and reduce the concentration of particles in the sample to a level which is acceptable to conventional measuring instruments. This effectively "freezes" the particle size distribution value upon entering the sample probe.

The sampling probe comprises:

(a) an outer tube having one end which terminates in a generally smooth tip for placement within a particle-laden gas stream and having at least one orifice in the sidewall near said tip for drawing a sample of gas from the stream;

(b) an inner tube located within said outer tube to form an annular space therebetween and a quenching zone between the inner tube end and said tip; and, optionally, (c) a plurality of baffles located within said inner tube and arranged to define a static mixing zone for mixing a stream of gas passed therethrough.

The dilution system typically is a closed, but not necessarily, recirculating system which is capable of providing a dilution gas to the quenching zone of the sampling probe through the annular space between the probe's inner and outer tubes. The sample of aerosol is quenched by dilution gas immediately as the sample enters the quenching zone, and almost simultaneously the sample, now partially diluted, is passed through the static mixing zone within the inner tube of the probe to achieve dilution and quenching to a concentration and temperature, respectively, suitable for measurement.

Typically, the dilution system will comprise a closed loop which communicates with the annular space of the sampling probe via an inlet nozzle for supplying dilution gas to the probe and with the inner tube of the probe via an exit nozzle for removing an appropriate amount of diluted and quenched gas from the probe for measurement. The loop will typically include:

(a) means for measuring the flow of dilution gas to the probe and for setting the circulation rate, such as, for example, a flow venturi;

(b) at least one filter for removing impurities (i.e., particles) from the dilution gas stream prior to its reaching the quenching zone of the probe;

(c) a dryer for removing unwanted moisture from the dilution gas;

(d) pumping means for supplying dilution gas to the quenching zone of the probe at an appropriate flow rate while simultaneously removing diluted and quenched gas from the probe; and (e) a make-up flow of dilution gas and an extraction flow of quenched gas to be measured which cooperate in operation to balance the pressure in the sampling system in relation to the pressure in the aerosol stream.

In a preferred embodiment, the sampling system further includes a solenoid valve, which provides an alternative to the continuous sampling of the aerosol. By opening and closing the solenoid at predetermined intervals during operation of the dilution system, intermittent sampling of the aerosol and time series dilution of the sample within the quenching zone is achieved. This feature is particularly advantageous when attempting to sample an aerosol stream which undergoes continuous pressure fluctuation, i.e., it provides for time series dilution which is much less susceptible to pressure variations within the moving aerosol stream from which a sample is to be taken. The pressure in the circulating loop raises above the highest pressures encountered in the process stream by adjusting the intake of clean gas, which is forced through the sampling orifice into the process stream at all times. The solenoid reduces the pressure in the circulating loop when it opens, i.e., the pressure in the probe falls below the pressure in the process stream and particles are sampled. Concomitantly, when the solenoid closes, the probe pressure increases and no more particles are sampled. The solenoid provides a pressure swing which overcomes any pressure fluctuations in the process stream. By controlling the ratio of the time the solenoid is opened to the time closed, the average dilution of the sample stream in turn can be controlled. With continuous operation, the baffles are used to vigorously dilute and quench the sample stream. When the process line pressure is near or above atmospheric pressure the preferred solenoid location is in a line on the dilution loop from a point on the sampling probe outer tube and communicating with the atmosphere. The advantage is rapid response time and short pulses. When the solenoid opens the pressure drops to atmospheric pressure. The sample flows into the orifice to make up the difference. If, however, the process line pressure is below atmospheric pressure, an optional pump may be connected to the outlet of the solenoid valve. Alternatively, when the process line pressure is below atmospheric pressure the solenoid location may be in a line parallel to said dilution loop and arranged so that the said valve communicates with two points on the dilution loop near the outlet nozzle of the probe. The advantage is the dilution line pressure is equal to process line pressure, however, a slower response time may result. The solenoid increases total flow with a parallel path when it is opened. The added flow is made up through the sampling orifice.

The present invention relates further to a method for continuously obtaining representative samples of particles from a hostile, concentrated aerosol stream for size and/or size distribution measurement in which the concentration of particles is greater than about $10^6$ particles/$cm^3$ which comprises:

(a) providing an enclosed quenching zone within said aerosol stream having at least one sampling orifice communicating therebetween;

(b) introducing samples of aerosol into said zone through said orifice by varying the pressure therein in relation to the pressure of said stream while simultaneously diluting the samples at a dilution ratio of at least about 500:1 by continuously passing a stream of dilution gas into said zone; and (c) immediately passing the diluted sample from said quenching zone to a mixing zone to dilute and cool the sample to a concentration and temperature, respectively, suitable for measurement.

The system and method of the invention provide a means for obtaining almost instantaneous values for particle size and particle size distribution for the aerosol which can then be correlated with quality parameters, and on-line quality control in the manufacture of fine particle products, such as, for example, pigmentary titanium dioxide, becomes possible.

BRIEF DESCRIPTION OF THE DRAWINGS

FIG. 1 is a cross sectional view of the sampling probe of the invention.

FIG. 2 is a cross sectional view of a second embodiment of the sampling probe.

FIG. 3A is a simplified schematic diagram of the sampling system of the invention when the process line pressure is near or above atmospheric pressure.

FIG. 3B is a simplified schematic diagram of the sampling system of the invention when the process line pressure is below atmospheric pressure.

DETAILED DESCRIPTION OF THE INVENTION

The aerosol sampling system of the invention comprises a sampling probe which operates in cooperation with a dilution system and is uniquely capable of obtaining representative particulate samples of the aerosol either intermittently or continuously from a moving aerosol stream where the particulate concentration of the aerosol is greater than about $10^6$ particles/$cm^3$. The sampling system is especially applicable for obtaining representative samples of particles from hostile aerosols, e.g., aerosol streams which are characteristic of continuous vapor state reactions in which the temperature of the gas stream can be as high as 1000° C., for example, or higher, and the particulate concentration can be as high as $10^{11}$ particles/$cm^3$, but seldom below $10^6$ particles/$cm^3$, and/or a corrosive chemical environment. Applicability will necessarily be limited by the materials available from which to make the probe.

Illustrative of such a process is the preparation of pigmentary titanium dioxide by oxidizing titanium tetrachloride in the vapor state with an oxygen-containing gas as described in greater detail in U.S. Pat. No. 2,488,439. Pure, vaporized, anhydrous titanium tetrachloride and an oxygen-containing gas, such as air, suitably enriched with from 0.1%-3% of water vapor, are separately and continuously introduced into a flame reactor wherein substantially complete oxidation of the titanium tetrachloride occurs at a temperature in the range of about 900°-1600° C. The gaseous reaction products contain $TiO_2$ in suspension and are subjected ordinarily to quick cooling to reduce their temperature below about 600° C. and prevent, or at least attempt to minimize, undesired growth taking place among the pigment particles by cementation or sintering of loosely-bound $TiO_2$ particles. Preferably, the finished pigment will have an average primary particle size radius ranging from 0.05 to 0.5 micron. Obtaining the appropriate size radius is accomplished usually by steam micronization. Available methods for particle size and size distribution measurement are not always capable of obtaining representative samples of pigment from the processing stream for immediate measurement. Samples are ordinarily taken from finished product inventory long after it is too late to make process corrections and prevent production of off-spec material. The system and method of the invention provide representative particulate samples almost instantaneously from the processing stream so that particle size and size distribution, two important quality control parameters, can be measured using conventional equipment, and process adjustments, such as a higher or lower steam input for micronization, can be made continuously during production.

Referring now to FIG. 1, the sampling probe 10, shown in partial section, is a generally elongated cylinder which comprises an outer tube 12 and an inner tube 14 located within the outer tube to form an annular space 16 therebetween through which can pass dilution gas. The outer tube 12 terminates at one end in a generally smooth tip 18 for placement within a particle-laden gas stream. Preferably the tip 18 is hemispherical in shape, as shown, to minimize turbulence. The inner tube 14 is located within the outer tube 12 to define a quenching zone 20 as the volume between the inner tube end 24 and the interior surface of the tip 18. At least one orifice 22 is located in close proximity to the quenching zone 20 and through which a sample of the aerosol to be measured can pass into the quenching zone. Preferably, the sampling orifice 22 is located within one outer tube diameter of the inner tube end 24 measured along the sidewall of the outer tube 12. The size of the orifice can vary depending on the diameter of aerosol particles to be sampled, but an orifice of 0.050 in. diameter (1.27 mm) will be satisfactory for most applications.

Within the interior of the inner tube 14 of the sampling probe are located a plurality of optional stationary baffles, or vanes 26, which are arranged along the length of the tube to define a static mixing zone. The number and arrangement of the vanes 26 depends on the maximum pressure drop which can be tolerated within the sampling system, i.e., through the sampling probe and dilution system. The configuration of the vanes 26 can be varied according to the gentleness of the mixing desired. In practice, the sampling probe functions as a counter current flow heat exchanger. Dilution air is introduced into the annular space 16 through an inlet nozzle 28 and flows along the length of the probe toward the quenching zone 20 to mix with and dilute a concentrated sample of aerosol being introduced through orifice 22. Almost simultaneously as dilution begins, the sample passes into the mixing zone where dilution and cooling of the sample to a concentration and temperature suitable for measurement occurs. The diluted sample exits the probe through exit nozzle 30.

Depending on processing conditions, e.g., temperature and pressure of the aerosol stream and particle concentration, the sampling probe may operate satisfactorily without the necessity of vanes 26 or baffles, i.e., the mixing capability may not be needed. In such a case, the sampling probe may, in fact, be less prone to clogging if the particle concentration is unusually high, and the system would require less overall maintenance and cleaning.

The length of the sampling probe is not especially critical. It should be long enough to conveniently reach near the central portion of the aerosol stream to be sampled, or at least long enough to obtain a representative sample from the aerosol stream and achieve cooling to the desired temperature.

Materials of construction for the probe are not especially critical. Their selection will depend on the temperature and chemical composition of the aerosol stream. Typically, a stainless steel alloy will be appropriate for most applications. Extremely high temperatures and/or a hostile chemical environment may require that a more corrosion resistant material be used, e.g., Hastelloy.

The sampling probe of the invention can be adapted as shown in greater detail in FIG. 2 for use in especially high temperature and/or corrosive applications, e.g., for sampling oxidation products directly downstream of the reaction zone in a flame reactor of the type typically used in the preparation of pigmentary titanium dioxide. A modified tip 32 is employed for insertion into the aerosol stream directly downstream of the reaction zone where temperatures are almost at their highest, e.g., in the range of about 900° to 1400° C. The tip can be modified as shown by a relatively abrupt tapering, or the tip can be more gently tapered at the convenience of the operator and achieve the same result. The annular space 16 and the quenching zone 20 volumes are somewhat enlarged to facilitate delivery of a larger volume of dilution air to the hot aerosol sample for more rapid cooling.

The orientation of the probe 10 within a moving aerosol stream is important to the extent the orifice 22 should be positioned within the stream where the flow characteristics are the smoothest. Generally speaking, the most turbulence will occur along the upstream and along the downstream surface of the probe 10 when the probe is placed perpendicularly with respect to the direction the aerosol stream is moving as shown in FIG. 2. Preferably, samples of the aerosol should be taken from regions of laminar flow, e.g., where the orifice 22 is positioned upward or downward along an axis which is perpendicular to the direction of flow. The probe 10 may have more than one sampling orifice 22, although no particular advantage has been observed.

Referring now to FIG. 3A and FIG. 3B, there are shown schematic diagrams, greatly simplified, of the sampling system of the invention. The sampling probe 10 operates in cooperation with a dilution system 34, which will typically, although not necessarily, comprise a means for measuring the flow of dilution gas to the probe and for setting the circulation rate, e.g., flow venturi 36, at least one filter 38 (Gelman Acroflow 11, 0.2 um), a dryer 40 (A silica gel or Drierite column which will allow a total flow of 1.5 cfm at less than 1" $H_2O$ pressure drop), and a main pump 42 which communicate via tubing 44, usually stainless steel tubing. The dilution system further comprises a solenoid valve 52A (shown on FIG. 3A) and a solenoid valve 52B (shown on FIG. 3B). FIG. 3A illustrates the solenoid valve location in the dilution loop which is preferred when the sampling system of the invention is used to sample an aerosol from a process line in which the process line pressure is near or above atmospheric pressure. The advantage is rapid response time and short pulses. If, however, the process line pressure 10 is below atmospheric pressure, an optional pump 54 may be connected to the outlet of the solenoid valve. When the solenoid opens, the pressure A drops to atmospheric pressure. FIG. 3B illustrates the alternate location for the solenoid valve when the process line pressure is below atmospheric pressure. The advantage is the dilution line pressure is equal to process line pressure, however, a slower response time may result. The dilution system 34 is operated typically as a closed, recirculating system in which the dilution gas comprises a mixture of the aerosol and ambient air which has been filtered and scrubbed of harmful components, i.e., components harmful to the measuring instruments to be used. Such a composition of dilution gas is advantageous as it resembles closely the particle environment of the aerosol to be sampled. The flow of dilution gas is maintained constant at about 20–30 l/sec at a dilution ratio which can range from 500:1 to 1000:1 or higher depending on the particulate concentration of the aerosol sample, temperature, etc.

The dilution system further comprises a make-up flow 46 of either ambient or process air, and an extraction flow 48 through which diluted representative samples are removed for measurement. The extraction flow line 48 will ordinarily include a ballast chamber 50 which reduces pressure fluctuations within the dilution system as samples are withdrawn. By changing the make-up flow and the extraction flow during operation of the sampling probe, it is possible to increase pressure within the dilution system. A controlled increase in pressure will usually result in a pulsing flow of dilution gas through the orifice from the quenching zone to the aerosol stream, i.e., a reverse pulsing flow which can be employed as necessary to clear particulate buildup around the sampling orifice.

Having successfully obtained a particulate sample for measurement using the invention, a number of measuring instruments are available which can measure particle size. For example, an Electrical Aerosol Size Analyzer, Model 3030 (available from TSI Instrument Co.), is an advanced electrostatic analyzer which can provide on-line aerosol size distribution measurements in less than two minutes. A Laser Aerosol Spectrometer, Model LAS-X (available from Particle Measuring Systems, Inc.), is an aerosol spectrometer designed to cover a size range of 0.09 to 3.0 microns. A built-in-printer provides automatic data logging of particle size spectra over a wide range of selectable sampling intervals from seconds to hours. Regardless of the instrument(s) to be used, calibrations must be conducted according to manufacturer's direction to insure satisfactory results.

The ability to obtain representative samples on-line from a hostile aerosol stream for particle size and size distribution measurement according to the invention can be coupled with means for correlating those values with product quality parameters for improved product quality control.

The terms and expressions which have been employed are used as terms of description and not of limitation, and there is no intention in the use of such terms and expressions of excluding any equivalent of the features shown and described or any portion thereof, but it is recognized that various modifications are possible within the scope of the invention claimed.

What is claimed is:

1. An improved system for obtaining representative samples of particles from an aerosol in which the particulate concentration of the aerosol is greater than $10^6$ particles/cm$^3$ which comprises a sampling probe arranged to operate in cooperation with a dilution system, said sampling probe comprising:
   (a) an outer tube having one end which terminates in a generally smooth tip for placement within a particle-laden aerosol stream and having at least one orifice in the sidewall near said tip for drawing a sample of aerosol from the stream;
   (b) an inner tube located within said outer tube to form an annular space therebetween and a quenching zone between the inner tube end and said tip; and
   (c) a mixing zone located within said inner tube; said dilution system comprising:
   (a) a loop which communicates with the annular space of the sampling probe via an inlet nozzle for supplying dilution gas to the probe and with the inner tube of the probe via an exit nozzle for removing an amount of diluted and quenched aerosol from the probe for measurement;
   (b) means within said loop for measuring the flow of dilution gas to the probe and for setting the circulation rate;
   (c) at least one filter within said loop for removing impurities from the dilution gas prior to its reaching the quenching zone of the probe;
   (d) pumping means within said loop for supplying dilution gas to the probe while simultaneously removing diluted and quenched gas from the probe; and
   (e) a make-up flow of dilution gas and an extraction flow of quenched gas to be measured which communicate with said loop and cooperate to balance the pressure in the sampling system in relation to the pressure within the aerosol stream being sampled.

2. The sampling system of claim 1 being adapted to sample an aerosol having a pressure which is less than, near to or more than atmospheric pressure further comprising a solenoid valve located in a line on the dilution loop from a point on the sampling probe outer tube and communicating with the atmosphere and arranged to open and close at predetermined intervals during sampling whereby intermittent sampling of the aerosol and time series dilution of the sample within the quenching zone is achieved.

3. The sampling system of claim 1 being adapted to sample an aerosol having a pressure less than atmospheric pressure further comprising a solenoid valve located in a line parallel to said dilution loop and arranged so that the said valve communicates with two points on the dilution loop near the outlet nozzle of the probe whereby opening and closing of said valve at predetermined intervals during sampling creates a change in system pressure whereby intermittent sampling of the aerosol and time series dilution of the sample within the quenching zone is achieved.

4. A method for continuously obtaining representative samples of particles from an aerosol stream in which the concentration of particles is greater than about $10^6$ particles/cm$^3$ which comprises:
   (a) providing an enclosed quenching zone within said aerosol stream with an outer tube having at least one sampling orifice therein and communicating therebetween;
   (b) introducing samples of said aerosol into said zone through said outer tube having the orifice therein by varying the pressure therein in relation to the pressure of said stream while simultaneously diluting the samples at a dilution ratio of at least about 500:1 by passing a stream of dilution gas into said zone; and
   (c) immediately passing the diluted sample through a mixing zone adjacent said quenching zone to dilute and cool the sample to a concentration and temperature, respectively, suitable for measurement.

* * * * *